United States Patent [19]
Gallo et al.

[11] 3,979,514
[45] *Sept. 7, 1976

[54] PROCESS FOR INTERRUPTING PREGNANCY WITH SULFONAMIDOAMINOPHENE INTERCEPTIVE AGENTS

[75] Inventors: Duane G. Gallo; William T. Comer, both of Evansville, Ind.

[73] Assignee: Mead Johnson & Company, Evansville, Ind.

[*] Notice: The portion of the term of this patent subsequent to July 6, 1993, has been disclaimed.

[22] Filed: Aug. 26, 1974

[21] Appl. No.: 500,809

[52] U.S. Cl. .............................. 424/244; 424/248; 424/274; 424/321
[51] Int. Cl.$^2$ .................................... A61K 31/33
[58] Field of Search ............ 424/244, 248, 274, 321

[56] References Cited
UNITED STATES PATENTS
3,341,584   9/1967   Larsen et al. ........................ 424/246

OTHER PUBLICATIONS

Uloth et al.; J. Med. Chem. 9 pp. 88–97 (1966).

Primary Examiner—Norman A. Drezin
Attorney, Agent, or Firm—Robert H. Uloth; Robert E. Carnahan

[57] ABSTRACT

A process for interrupting pregnancy is disclosed which comprises administration to a mammal an interceptive agent selected from a group of sulfonamidoaminophenones. Illustrative of sulfonamidoaminophenone interceptive agents useful in the process of the present invention for interrupting pregnancy are 4'-(N,N-diethylalanyl)methanesulfonanilide and 4'-[N-α,α-dimethylphenethyl)alanyl]methanesulfonanilide.

14 Claims, No Drawings

PROCESS FOR INTERRUPTING PREGNANCY WITH SULFONAMIDOAMINOPHENE INTERCEPTIVE AGENTS

BACKGROUND OF THE INVENTION

This invention relates to drug and body treating compositions and is particularly concerned with a process for interrupting pregnancy after implantation of the fertilized ovum has taken place by administration of a p-sulfonamidoaminophenone interceptive agent.

At the present time, there are a number of available oral contraceptives containing estrogenic and progestational steroids that inhibit pregnancy by preventing ovulation if administered on an almost daily regimen. But, after fertilization and implantation of the ovum has taken place, there is presently little, short of mechanical (vacuum aspiration) or surgical abortion, that can be done to prevent delivery of viable offspring. Thus, there remains a large unmet need for a safe medication which requires infrequent or at the most only short periods of treatment to induce elimination of unwanted embryos. For the purpose of this disclosure, agents that interrupt pregnancy after implantation of the fertilized ovum are called "interceptives" as opposed to the term "contraceptives" which applies to agents that prevent pregnancy by inhibiting conception; refer to R. H. Naqvi, et al., Steroids, 18:731, 1971.

A few of the p-sulfonamidoaminophenones useful in the present invention are specifically disclosed by A. A. Larsen, et al., U.S. Pat. No. 3,341,584 to be of value as central nervous system agents. It was not recognized, however, until the present discovery that some of the p-sulfonamidoaminophenones disclosed by Larsen, et al. as well as other novel compounds of that class are effective interceptive agents.

SUMMARY OF THE INVENTION

This invention is concerned with a process for interrupting pregnancy in a mammal. In particular, the invention relates to the use of p-sulfonamidoaminophenones of Formula I below to interrupt pregnancy after implantation has taken place. Non-toxic pharmaceutically acceptable acid addition salts of the compounds of Formula I are also effective in the process of the invention.

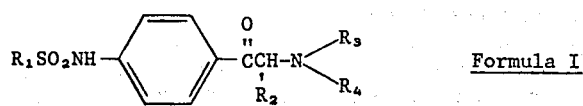

Formula I

In Formula I, $R_1$ is methyl or ethyl, $R_2$ is selected from the group of alkyl radicals having 1 to 3 carbon atoms inclusive. Said alkyl radicals can be straight chained or branched. The substituent $R_3$ can be hydrogen, straight or branched chain lower alkyl of 1 to 4 carbon atoms inclusive or benzyl. $R_4$ can also be straight or branched chain lower alkyl of 1 to 5 carbon atoms inclusive, but in addition represents aralkyl groups of up to 15 carbon atoms inclusive, haloaralkyl groups of up to 15 carbon atoms inclusive, allyl, 2-propynyl, adamantyl, and cycloalkyl radicals of 3 to 6 carbon atoms inclusive. The $R_3$ and $R_4$ substituents taken together with the nitrogen atom to which they are attached represent moieties selected from morpholino, thiomorpholino, or heteromonocyclics having from 4 to 8 carbon atoms inclusive wherein said heteromonocyclic moieties may be unsubstituted or substituted with up to 2 methyl radicals.

The term "non-toxic pharmaceutically acceptable acid addition salts" as used herein refers to salts of the sulfonamidoaminoketones of Formula I with relatively non-toxic inorganic or organic acids. Illustrative of non-toxic pharmaceutically acceptable acid addition salts of compounds characterized by Formula I are the salts of inorganic or organic acids such as sulfuric, phosphoric, hydrochloric, hydrobromic, hydroiodic, sulfamic, acetic, lactic, malic, succinic, maleic, fumaric, tartaric, citric, gluconic, glutaric, ascorbic, benzoic, cinnamic, methanesulfonic, ethanesulfonic, p-toluenesulfonic, isethionic, and other related acids.

Preparation of pharmaceutically acceptable acid addition salts of the compounds of Formula I is accomplished by admixture of the sulfonamidoketone bases with at least one chemical equivalent of any of the various acids hereinabove listed. Generally, the salts are prepared in a reaction inert solvent such as ether, benzene, ethanol, methanol ethyl acetate, acetone, acetonitrile, chloroform, water and the like.

Compounds characterized by Formula I which are useful in the process of the present invention are prepared by reaction of a sulfonamidohaloketone of Formula II

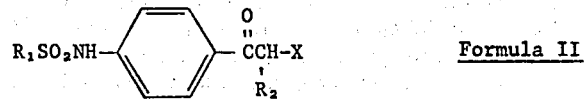

Formula II with an amine of Formula III

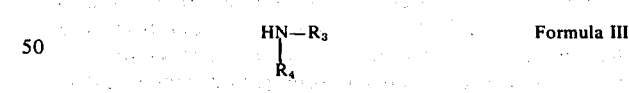

Formula III

In Formulas II and III above, $R_1$, $R_2$, $R_3$ and $R_4$ have the meanings hereinabove given for Formula I while the symbol "X" comprehends halogen including chlorine, fluorine and iodine and, preferably, bromine.

Illustrative of Formula II reactants which can be reacted with amines of Formula III are:

4'-(2-bromoacetyl)methanesulfonanilide,
4'-(2-chloroacetyl)methanesulfonanilide,
4'-(2-bromopropionyl)methanesulfonanilide,
4'-(2-bromopropionyl)ethanesulfonanilide.

Illustrative of amine reactants of Formula III which can be reacted with sulfonamidohaloketones of Formula II are:

diethylamine,
isopropylamine, tert.-butylamine,
1,1-dimethylpropylamine,
1-ethylpropylamine,
N-methylbenzylamine,
N-isopropylbenzylamine,
N-methylallylamine,
N-methylpropynylamine,
hexamethylenimine,
pyrrolidine,
morpholine,
thiomorpholine,
adamantylamine,
dibenzylamine,
benzhydrylamine,
3,3-diphenylpropylamine,
α,α-dimethylphenethylamine,
4-chloro-α,α-dimethylphenethylamine,
4-bromo-α,α-dimethylphenethylamine,
4-fluoro-α,α-dimethylphenethylamine.

Reaction of the sulfonamidohaloketones of Formula II with primary or secondary amines of Formula III is preferably carried out in protic or aprotic reaction inert solvents. The term "reaction inert solvent" as used herein is intended to refer to those solvents which act as a diluent for the reaction but themselves do not combine with the reactants. Acetonitrile is a particularly preferred reaction inert solvent for carrying out the preparation of the compounds of Formula I but other solvents such as ethanol, ethyl acetate, dimethoxyethane, benzene, tetrahydrofuran, 1,1-dichloroethane and the like are also satisfactory. Two molar equivalents of an amine of Formula III to one molar equivalent of a sulfonamidohaloketone of Formula II are generally employed since one molar equivalent of amine acts as an acid scavenger to take up the hydrohalide by-product of the reaction. Condensation of the sulfonamidohaloketones of Formula II and Formula III reactants are carried out at temperatures ranging from −10° to 80°C. The temperature at which the reaction is conducted is not particularly critical and the reaction is complete in from 0.5 to 48 hrs. In general, the required time period to complete the reaction is inversely proportional to the temperature at which the reaction is conducted, i.e., the higher the reaction temperature, the shorter the reaction period.

According to the process of the present invention for interrupting pregnancy, the compounds of Formula I and pharmaceutically acceptable acid addition salts thereof are administered in effective doses orally or parenterally, e.g., by intramuscular, intravenous, intraperitoneal, or subcutaneous injection, to a pregnant mammal during a critical stage of embryonic development wherein the embryo is subject to interception in an effective dose to interrupt pregnancy. For the purpose of this disclosure, the "critical stage of embryonic development wherein the embryo is subject to interception" referred to herein is also designated the "interceptive stage".

The term "effective dose" used herein refers to the amount of an interceptive agent of Formula I which is required to interrupt pregnancy when administered during the interceptive stage which occurs at a specific time for each species after implantation of the fertilized ovum. The amount of an "effective dose" ranges from 20 to 500 mg./kg. body weight. Preferably an effective amount of an interceptive agent of Formula I is administered in a single dose to interrupt pregnancy, but multiple dosing can also be employed if desired. For instance, doses which themselves are not completely effective can be administered over a period of several days to achieve the desired effect. It will be recognized by those skilled in the art that the dosage of the sulfonamidoaminophenones of Formula I employed in carrying out the process of the present invention for interrupting pregnancy in mammals will vary with the form and mode of administration, with the species of mammal, and to some degree with the particular interceptive agent chosen. Dosage figures given herein refer to the dose of "active ingredient" which is a term applied to the Formula I free bases. When employing an acid addition salt of the aminoketones of Formula I, the size of the dose is adjusted to take into account the percent of active ingredient contained in the salt.

Compounds particularly preferred for practicing the process of the present invention are:
  4'-[N-(4-chloro-α,α-dimethylphenethyl)alanyl]methanesulfonanilide,
  4'-[N-(α,α-dimethylphenethyl)alanyl]methanesulfonanilide,
  4'-(N,N-diethylalanyl)methanesulfonanilide,
  4'-(N-benzyl-N-methylalanyl)methanesulfonanilide,
  4'-[2-(hexahydro-1H-azepin-1-yl)propionyl]methanesulfonanilide,
  4'-(N-allyl-N-methylalanyl)methanesulfonanilide,
  4'-(N-isopropyl-N-methylalanyl)methanesulfonanilide,
  4'-[2-(1-pyrrolidinyl)propionyl]methanesulfonanilide,
  4'-(N-tert.-butylalanyl)methanesulfonanilide.

The interceptive agents of Formula I and their pharmacologically acceptable acid addition salts are relatively non-toxic and substantially free from other pharmacological effects upon oral or parenteral administration to a mammal at doses which produce the interceptive effect. $LD_{50}$ values in mice for 4'-(N,N-diethylalanyl)methanesulfonanilide hydrochloride are 1514 mg./kg. orally and 746 mg./kg. intraperitoneally. In the rat and rhesus monkey, the oral $LD_{50}$ value for 4'-(N,N-diethylalanyl)methanesulfonanilide hydrochloride is 2347 mg./kg. and greater than 800 mg./kg. respectively.

To determine the critical embryonic stage in a mammal following fertilization wherein embryonic development may be intercepted, i.e., the interceptive stage, an interceptive agent of Formula I is administered to different groups of animals at various times after implantation of the fertilized ovum in accord with accepted pharmacological procedures. For example, a maximally tolerated dose of the interceptive agent is administered to a pregnant mammal at intervals related to the duration of gestation of the species being investigated beginning after implantation in accordance with the schedule suggested in Table I with a subsequent determination of whether pregnancy has been interrupted.

TABLE I

SUGGESTED FREQUENCY OF DOSING TO DETERMINE INTERCEPTIVE STAGE

| Gestation Length | Initial Dose After Implantation | Interval |
|---|---|---|
| 30 days | 3 days | 2 days |
| 31–60 days | 5 days | 3 days |
| 61–160 days | 8 days | 4 days |
| greater than 160 days | 12 days | weekly |

In lower mammals such as the mouse, rat, hamster, rabbit, guinea pig, interruption of pregnancy is established by autopsy. In more valuable mammals such as the pig, cow, dog, and higher primates including the human, interruption of the pregnancy can be readily determined by such means as transcervical examination of the uterine wall, laproscopic examination, rectal palpation of the uterus, and in higher primates onset of menses, all of which can be, if desired, supplemented with determination of urinary and/or blood pregnancy associated hormone levels. After the "interceptive stage" is established, the minimally effective dose can be determined, if desired, by administering various doses of the interceptive agent in accord with standard pharmacological procedures.

The interceptive stage of embryonic development for representative mammalian species determined by oral administration of 4'-(N,N-diethylalanyl)methanesulfonanilide as described hereinabove is given in Table II.

TABLE II

APPROXIMATE INTERCEPTIVE STAGE OF EMBRYONIC DEVELOPMENT

| Mammalian Species | Days Following Fertilization |
|---|---|
| Rat | 10–12 |
| Mouse | 10–12 |
| Hamster | 9–15 |
| Rabbit | 11–18 |
| Guinea Pig | 14–34 |

In higher primates, the process of the invention may also be considered a process for inducing menses. In this instance, absence of a menstrual flow is considered indicative of pregnancy and menses is induced by administering an effective dose of compounds of Formula I commencing 1 to 2 weeks after the expected onset of menstrual flow.

Interceptive agents characterized by Formula I can be employed in admixture with the usual pharmaceutical carriers in carrying out the process of the present invention for interrupting pregnancy. Those organic and inorganic pharmaceutical carrier substances suitable for oral and parenteral application such as water, vegetable oils, polyethylene glycol, gelatin, lactose, starch, magnesium stearate, talc, and the like are operable. For oral administration, tablets, capsules, powders, granules, syrups, elixirs, liquid suspensions, or solutions are preferred. The interceptive agents of Formula I can be incorporated with a pharmaceutical carrier in unit dosages providing from 250 to 2000 mg. of active ingredient and effective amounts thereof are administered to mammals in practicing the process of the present invention for interrupting pregnancy.

The following examples are given to further illustrate the present invention. They are merely illustrative and are not to be construed as limiting the scope of the claims in any manner whatsoever.

DESCRIPTION OF SPECIFIC EMBODIMENTS

EXAMPLE 1

EFFECT OF A SINGLE ORAL DOSE OF 4'-(N,N-DIETHYLALANYL)METHANESULFONANILIDE HYDROCHLORIDE ON PREGNANCY RATE IN THE RAT, MOUSE, RABBIT, HAMSTER AND GUINEA PIG

Mature female rats of the Harlan-Wister strain weighing between 200 and 300 g. were mated to males of the same strain and divided into groups of 10. For the purpose of this experiment, day 1 of pregnancy was designated as that day on which sperm were first observed in a vaginal smear after caging the animals together. Animals of one group served as a control while varying doses of 4'-(N,N-diethylalanyl)methanesulfonanilide hydrochloride in an appropriate pharmaceutical vehicle such as water were administered orally to other groups on day 11 (the day of pregnancy midway in the interceptive stage of embryonic development). The animals were sacrificed a suitable period after dosing such as 5–10 days and the uteri were examined for the number and condition of implantation sites. Animals exhibiting at least one normal implantation site were considered to be pregnant, while those showing no evidence of an implantation site were excluded from the experiment. The foregoing procedure was repeated with rabbits except that ovulation was artificially induced by injected human chorionic gonadotropin and pregnancy induced by artificial insemination. Results obtained are listed below:

| Mammal | Day of Pregnancy Administered | Oral Dose (mg./kg.) | Percent Pregnant |
|---|---|---|---|
| Mouse | 11 | 0 | 100 |
|  |  | 250 | 86 |
|  |  | 375 | 33 |
|  |  | 500 | 0 |
| Rat | 11 | 0 | 100 |
|  |  | 84 | 100 |
|  |  | 167 | 86 |
|  |  | 251 | 29 |
|  |  | 335 | 0 |
| Rabbit | 15 | 0 | 100 |
|  |  | 25 | 100 |
|  |  | 50 | 38 |
|  |  | 100 | 11 |
|  |  | 150 | 0 |
| Hamster | 12 | 0 | 100 |
|  |  | 100 | 100 |
|  |  | 200 | 40 |
|  |  | 250 | 0 |
| Guinea Pig | 23 | 0 | 100 |
|  |  | 100 | 40 |
|  |  | 250 | 0 |

EXAMPLES 2–5

Results are given below for other representative sulfonamidophenone hydrochloride salts of Formula I administered orally as a single dose to rats on day 11 of pregnancy in accordance with the procedure of Example 1.

| Ex. No. | Interceptive Agent | Dose Millimole/kg. | % Pregnant |
|---|---|---|---|
| 2 | 4'-[N-(4-chloro-α,α-dimethylphenethyl)alanyl]methanesulfonanilide | 0 | 100 |
|  |  | 0.125 | 50 |
|  |  | 0.25 | 0 |
| 3 | 4'-[N-α,α-dimethylphenethyl)alanyl]methanesulfonanilide | 0 | 100 |
|  |  | 0.25 | 89 |
|  |  | 0.5 | 12 |

-continued

| Ex. No. | Interceptive Agent | Dose Millimole/kg. | % Pregnant |
|---|---|---|---|
| 4 | 4'-(N-benzyl-N-methylalanyl)-methanesulfonanilide | 0.75 | 0 |
| | | 0 | 100 |
| | | 0.25 | 100 |
| | | 0.5 | 40 |
| | | 0.75 | 0 |
| 5 | 4'-[2-(hexahydro-1H-azepin-1-yl)propionyl]methanesulfonanilide | 0 | 100 |
| | | 0.25 | 89 |
| | | 0.5 | 71 |
| | | 0.75 | 25 |
| | | 1.0 | 0 |

EXAMPLES 6–22

Additional examples of p-sulfonamidoaminoketone interceptive agents of Formula I useful in the process of the present invention for interrupting pregnancy as demonstrated by administration of a single oral dose to the rat in accordance with the procedure of Example 1 are listed below:

| Ex. No. | Interceptive Agent |
|---|---|
| 6 | 4'-(N-allyl-N-methylalanyl)methanesulfonanilide |
| 7 | 4'-(N-isopropyl-N-methylalanyl)methanesulfonanilide |
| 8 | 4'-[2-(1-pyrrolidinyl)propionyl]methanesulfonanilide |
| 9 | 4'-(N-tert.-butylalanyl)methanesulfonanilide |
| 10 | 4'-[2-(isopropylamino)butyryl]methanesulfonanilide |
| 11 | 4'-(2-morpholinopropionyl)methanesulfonanilide |
| 12 | 4'-[N-methyl-N-(2-propynyl)alanyl]methanesulfonanilide |
| 13 | 4'-[N-(1-adamantyl)alanyl]methanesulfonanilide |
| 14 | 4'-(2-dibenzylaminopropionyl)methanesulfonanilide |
| 15 | 4'-(N,N-dimethylalanyl)methanesulfonanilide |
| 16 | 4'-[(N-benzyl-N-isopropyl)alanyl]methanesulfonanilide |
| 17 | 4'-[N-(diphenylmethyl)alanyl]methanesulfonanilide |
| 18 | 4'-(N-cyclopentylalanyl)methanesulfonanilide |
| 19 | 4'-[N-(3,3-diphenylpropyl)alanyl]methanesulfonanilide |
| 20 | 4'-[N-(1,1-dimethylpropyl)alanyl]methanesulfonanilide |
| 21 | 4'-(N-isopropylalanyl)methanesulfonanilide |
| 22 | 4'-(isopropylaminoglycyl)methanesulfonanilide |

Preparation of Aminoketones

Procedures for the preparation of the compounds of the present invention characterized by Formula I are disclosed in A. A. Larsen, et al., U.S. Pat. No. 3,341,584 and R. H. Uloth, et al., J. Med. Chem., 9, 88 (1966). However, in order to assure that Formula I aminoketones employed in the present invention are readily available to those persons desiring to practice the interceptive process of the present invention, preparation of representative aminoketones of Formula I are given below.

Compound 1

Diethylamine (21.9 g., 0.3 mole) in 50 ml. of acetonitrile is added to 4'-(2-bromopropionyl)methanesulfonanilide (30.6 g., 0.1 mole) in 200 ml. of acetonitrile over a period of 2 minutes. The reaction mixture is refluxed for 30 min., concentrated to about one-half volume and filtered. Dilution of the filtrate with about 600 ml. of ether provides a precipitate of diethylamine hydrobromide by-product which is collected and washed with ether. Acidification of the combined filtrate and ether wash with ethanolic hydrogen chloride affords an oily precipitate. After separating the oily precipitate by decantation, 200 ml. of acetone is added to provide a white solid which is collected, washed with acetone and air dried yielding 29.0 g. of white solid, m.p. 175°–180°C. Crystallization of this product from methanol-isopropyl alcohol provides analytically pure 4'-(N,N-DIETHYLALANYL)METHANESULFONANILIDE HYDROCHLORIDE, m.p. 184.0°–187.0°C. (corr.).

Analysis. Calcd. for $C_{14}H_{22}N_2O_3S \cdot HCl$: C, 50.22; H, 6.92; N, 8.36. Found: C, 50.41; H, 7.03; N, 8.09.

Compound 2

A mixture of 4'-(2-bromopropionyl)methanesulfonanilide (15.3 g., 0.05 mole) and 4-chloro-α,α-dimethylphenethylamine (18.4 g., 0.1 mole) in 200 ml. of acetonitrile is refluxed for a period of 24 hr. The product is isolated by filtering the reaction mixture, concentrating the filtrate to a small volume, diluting the concentrate with ether, filtering and washing the filtrate with water. The ethereal solution is dried over magnesium sulfate, filtered and the filtrate containing the free base acidified with ethanolic hydrogen chloride affords the hydrochloride salt. The crude hydrochloride salt crystallized from methanol-isopropyl alcohol and dried provides analytically pure 4'-[N-(4-CHLORO-α,α-DIMETHYLPHENETHYL)ALANYL]METHANESULFONANILIDE HYDROCHLORIDE, m.p. 228.0°–233.0°C. (dec.)(corr.).

Analysis. Calcd. for $C_{20}H_{25}ClN_2O_3S \cdot HCl$: C, 53.93; H, 5.88; N, 6.29. Found: C, 53.93; H, 5.91; N, 6.11.

Compound 3

A mixture of 4'-(2-bromopropionyl)methanesulfonanilide (15.3 g., 0.05 mole) and α,α-dimethylphenethylamine (16.42 g., 0.11 mole) in 200 ml. of acetonitrile is refluxed for a period of 16 hr. The product is isolated by concentrating the reaction mixture under reduced pressure, dissolving the residue in chloroform which is then washed with water, dried over magnesium sulfate, filtered through diatomaceous earth and concentrated to provide an oily residue of the crude product free base. The residue is taken up in butanone, acidified with ethanolic hydrogen chloride and the insoluble hydrochloride salt product collected, washed with butanone and dried. Crystallization of the hydrochloride salt from methanol-isopropyl alcohol and drying at high vacuum affords analytically pure 4'-[N-α,α-DIMETHYLPHENETHYL)-ALANYL]-METHANESULFONANILIDE HYDROCHLORIDE, m.p. 236.0°–237.0°C. (dec.).

Analysis. Calcd. for $C_{20}H_{26}N_2O_3S \cdot HCL$: C, 58.45; H, 6.62; N, 6.82. Found: C, 58.45; H, 6.98; N, 6.79.

Compound 4

A mixture of 4'-(2-bromopropionyl)methanesulfonanilide (30.6 g., 0.1 mole) and N-methylbenzylamine (24.0 g., 0.2 mole) in 400 ml. of acetonitrile is stirred for 16 hr. at room temperature and then concentrated under reduced pressure. The desired product is isolated by stirring the residue thus obtained with 500 ml. of warm acetone, filtering and concentrating the acetone extract under pressure to provide a yellow solid which crystallized from ethanol affords 14 g. of the product free base, m.p. 163°–169°C. (dec.). The free base is further purified by dissolving in 100 ml. of 1 N hydrochloric acid, filtering and reprecipitating the free base by neutralizing the filtrate with concentrated ammonium hydroxide. The free base is collected, dried and crystallized from methanol to yield analytically pure 4'-[N-BENZYL-N-METHYL)ALANYL]METHANESULFONANILIDE, m.p. 173.5°–176.5°C.

(corr.). The free base is converted to the hydrochloride salt and obtained analytically pure by crystallization from methanol-isopropyl alcohol, m.p. 211.0°–214.0°C. (corr.).

Analysis. Calcd. for $C_{18}H_{22}N_2O_3S.HCl$: C, 56.46; H, 6.05; N, 7.32. Found: C, 56.64; H, 6.03; N, 7.15.

Compound 5

A mixture of 4'-(2-bromopropionyl)methanesulfonanilide (15.3 g., 0.05 mole) and hexamethyleneimine (9.92 g., 0.1 mole) in 200 ml. of acetonitrile is refluxed for a period of 16 hr. and filtered. The desired product is isolated by concentrating the filtrate to a volume of about 75 ml., diluting with a ten-fold amount of ether and filtering. Acidification of the filtrate containing the soluble free base product with ethanolic hydrogen chloride provides the hydrochloride salt. Crystallization of the hydrochloride salt from methanol-isopropyl alcohol yields analytically pure 4'-[2-(HEXAHYDRO-1H-AZEPIN-1-YL)PROPIONYL]-METHANESULFONANILIDE HYDROCHLORIDE, m.p. 236.0°–240.0°C. (dec.).

Analysis. Calcd. for $C_{16}H_{24}N_2O_3S.HCl$: C, 53.25; H, 6.98; N, 7.32. Found: C, 53.12; H, 7.23; N, 7.63.

Compound 6

A mixture of 4'-(2-bromopropionyl)methanesulfonanilide (15.3 g., 0.05 mole) and N-methylallyamine (7.82 g., 0.11 mole) in 200 ml. of acetone is refluxed for a period of 3 hr. The desired product is isolated by filtering the reaction mixture, concentrating the filtrate, dissolving the residue thus obtained in chloroform, washing the chloroform solution with water, drying over magnesium sulfate, and concentrating to provide the free base. The hydrochloride salt of the aminoketone product is prepared and crystallized from methanol-isopropyl alcohol to afford analytically pure 4'-(N-ALLYLN-METHYLALANYL)METHANESULFONANICIDE HYDROCHLORIDE, m.p. 209.0°–211.0°C. (corr.).

Analysis. Calcd. for $C_{14}H_{20}N_2O_3S.HCl$: C, 50.52; H, 6.36; N, 8.42. Found: C, 50.62; H, 6.55; N, 8.14.

Compound 7

A mixture of 4'-(2-bromopropionyl)methanesulfonanilide (15.3 g., 0.05 mole) and N-methylisopropylamine (7.3 g., 0.1 mole) in 250 ml. of acetonitrile is refluxed for 1 hr. and then stirred at room temperature for a period of 16 hr. The desired product is isolated by concentrating the reaction mixture to about 1/3 volume, diluting with about 800 ml. of ether, and filtering. Acidification with ethanolic hydrogen chloride provides an oily precipitate of the hydrochloride salt which is separated by decantation and triturated with acetone to yield analytically pure 4'-(N-ISOPROPYL-N-METHYLALANYL)-METHANESULFONANILIDE HYDROCHLORIDE HEMIHYDRATE, m.p. 197.5°–203.5°C. (corr.).

Analysis. Calcd. for $C_{14}H_{22}N_2O_3S.HCL.\frac{1}{2}H_2O$: C, 48.90; H, 7.03; N, 8.15. Found: C, 48.83; H, 6.95; N, 7.98.

Compound 8

A mixture of 4'-(2-bromopropionyl)methanesulfonanilide (15.3 g., 0.05 mole) and pyrrolidine (8.9 g., 0.125 mole) in 125 ml. of acetonitrile is refluxed for a period of 1 hr. The desired product is isolated by concentrating the reaction mixture to an oil, dissolving the oil in acetonitrile, filtering and acidifying the filtrate with ethanolic hydrogen chloride to provide the hydrochloride salt which is collected, washed with acetonitrile, dried and crystallized from ethanol yielding analytically pure 4'-[2-(1-PYRROLIDINYL)PROPIONYL]-METHANESULFONANILIDE HYDROCHLORIDE MONOHYDRATE, m.p. 230.0°–233.0°C. (dec.)-(corr.).

Analysis. Calcd. for $C_{14}H_{20}N_2O_3S.HCl.H_2O$: C, 47.93; H, 6.61; N, 7.98. Found: C, 47.92; H, 6.28; N, 7.89.

Following the above procedure but substituting an equimolar amount of 2-methylpyrrolidine or 2,2-dimethylpyrrolidine for pyrrolidine there is obtained respectively 4'-[2-(2-METHYL-1-PYRROLIDINYL)PROPIONYL]-METHANESULFONANILIDE and 4'-[2-(2,2-DIMETHYL-1-PYRROLIDINYL)PROPIONYL]-METHANESULFONANILIDE.

Compound 9

A mixture of 4'-(2-bromopropionyl)methane-sulfonanilide (30.6 g., 0.1 mole) and tert.-butylamine (67.0 g., 0.92 mole) in 200 ml. of acetonitrile is refluxed for a period of 16 hr., diluted with ether and filtered. The filter cake consisting of a mixture of the product free base and the by-product tert.-butylamine hydrobromide is triturated with acetonitrile and the relatively less soluble free base collected. The crude free base is further purified by preparing the hydrochloride salt which is crystallized from methanolether to provide analytically pure 4'-(N-tert.-BUTYLALANYL)METHANE-SULFONANILIDE HYDROCHLORIDE MONOHYDRATE, m.p. 255.5°–256.5°C. (dec.).

Analysis. Calcd. for $C_{14}H_{22}N_2O_3S.HCl.H_2O$: C, 47.65; H, 7.14; N, 7.94. Found: C, 48.02; H, 7.12; N, 7.99.

Compound 10

A mixture of 4'-(2-bromobutyryl)methanesulfonanilide (22.4 g., 0.07 mole) and isopropylamine (16.5 g., 0.28 mole) in 100 ml. of acetonitrile is stirred at ice bath temperature for 1 hr. and then at room temperature for a period of 16 hr. The product is isolated by concentrating the reaction mixture under reduced pressure, triturating the residue with water and filtering. The filter cake containing the free base is taken up in acetone and the hydrochloride salt prepared by the addition of ethanolic hydrogen chloride. The crude hydrochloride salt crystallized from methanol-acetone provides analytically pure 4'-[(2-ISOPROPYLAMINO)BUTYRYL]METHANESULFONANILIDE HYDROCHLORIDE, m.p. 214.0°–221.0°C. (dec.)(corr.).

Analysis. Calcd. for $C_{14}H_{22}N_2O_3S.HCl$: C, 50.22; H, 6.93; N, 8.36. Found: C, 50.41; H, 7.09; N, 8.18.

Compound 11

A mixture of 4'-(2-bromopropionyl)methanesulfonanilide (15.3 g., 0.05 mole) and morpholine (8.7 g., 0.1 mole) in 500 ml. of acetonitrile is refluxed for a period of 1 hr. The desired product is isolated by filtering the reaction mixture, concentrating the filtrate to an oil, dissolving the residual oil in 1:1 ether-water mixture, separating the ether layer, drying the ether extract over magnesium sulfate, filtering and acidifying the filtrate with ethanolic hydrogen chloride to afford the crude hydrochloride salt as an oil. The crude hydrochloride is separated by decantation, tritiated with acetone and crystallized from methanol-isopropyl alcohol to provide analytically pure 4'-[2-(MORPHOLINO)PROPIONYL]METHANESULFONANILIDE HYDROCHLORIDE, m.p. 236.0°–238.0°C. (dec.)(corr.).

Analysis. Calcd. for $C_{14}H_{20}N_2O_4S \cdot HCl$: C, 48.20; H, 6.07; N, 8.03. Found: C, 48,42; H, 6.01; N, 8.03.

Compound 12

A mixture of 4'-(2-bromopropionyl)methane-sulfonanilide (15.3 g., 0.05 mole) and N-methylpropargylamine (7.6 g., 0.11 mole) in 200 ml. of acetonitrile is refluxed for a period of 3 hr. then concentrated under reduced pressure. The resulting residue is triturated with water and then taken up in 200 ml. of acetone. The dried acetone solution (magnesium sulfate) is acidified with ethanolic hydrogen chloride and diluted with ether to provide 4'-[(N-METHYL-N-(2-PROPYNYL)ALANYL]METHANESULFONANILIDE HYDROCHLORIDE which is crystallized from methanol-isopropyl alcohol to analytical purity, m.p. 212.0°–215.0°C. (corr.).

Analysis. Calcd. for $C_{14}H_{18}N_2O_3S \cdot HCl$: C, 50.83; H, 5.79; N, 8.47. Found: C, 50.60; H, 5.76; N, 8.35.

Compound 13

A mixture of 4'-(2-bromopropionyl)methanesulfonanilide (12.85 g., 0.042 mole) and adamantanamine (12.7 g., 0.084 mole) in 200 ml. of acetonitrile is refluxed for a period of 4 hr. and then stirred at room temperature overnight. The desired product is isolated by filtering the reaction mixture, concentrating the filtrate under reduced pressure, triturating the residue thus obtained with acetone, filtering, and acidifying the filtrate with ethanolic hydrogen chloride to provide the hydrochloride salt. Crystallization of the hydrochloride salt from methanol-isopropyl ether affords analytically pure 4'-[N-(1-ADAMANTYL)ALANYL]METHANESULFONANILIDE HYDROCHLORIDE, m.p. 239.0°–242.0°C. (dec.)(corr.).

Analysis. Calcd. for $C_{20}H_{28}N_2O_3S \cdot HCl$: C, 58.17; H, 7.08; N, 6.78. Found: C, 58.36; H, 7.27; N, 6.62.

Compound 14

Reaction of 4'-(2-bromopropionyl)methanesulfonanilide with 2 molar equivalents of dibenzylamine in acetonitrile provides 4'-(N,N-DIBENZYLALANYL)-METHANESULFONANILIDE purified as the hydrochloride, m.p. 216.0°–218.0°C. (dec.).

Analysis. Calcd. for $C_{24}H_{26}N_2O_3S \cdot HCl$: C, 62.80; H, 5.93; N, 6.10. Found: C, 62.47; H, 5.91; N, 6.10.

Compound 15

A mixture of 40'-(2-bromopropionyl)methanesulfonanilide (15.3 g., 0.05 mole) and dimethylamine (9.02 g., 0.2 mole, 25% in water) in 250 ml. of acetonitrile is stirred for a period of 16 hr. The product is isolated by concentrating the reaction mixture, diluting the residue thus obtained with ether, filtering, acidifying the filtrate with ethanolic hydrogen chloride, decanting, the ether solvent, and triturating the oily residue with acetone. The product hydrochloride crystallized first from ethanol and then from methanol-isopropyl alcohol affords analytically pure 4'-(N,N-DIMETHYLALANYL)METHANESULFONANILIDE HYDROCHLORIDE HEMIHYDRATE, m.p. 204.5°–207.5°C. (corr.).

Analysis. Calcd. for $C_{12}H_{18}N_2O_3S \cdot HCL \cdot \tfrac{1}{2}H_2O$: C, 45.64; H, 6.38; N, 8.87. Found: C, 45.54; H, 6.17; N, 8.84.

Compound 16

A mixture of 4'-(2-bromopropionyl)methanesulfonanilide (15.3 g., 0.05 mole) and N-isopropylbenzylamine (14.92 g.,) 0.1 mole) in 200 ml. of acetonitrile is refluxed for a period of 16 hr. The product is isolated by filtering the reaction mixture, concentrating the filtrate, dissolving the residue thus obtained in chloroform, washing the chloroform extract with water, drying over magnesium sulfate, and concentrating the dried chloroform solution and reduced pressure to afford the crude free base as an oil. The oily free base is purified by dissolving in methanol, passing through a silica-gel column (eluting with chloroform). The chloroform eluate is concentrated under reduced pressure to provide the crude free base which is further purified by crystallization from ethyl acetate-n-hexane affording analytically pure 4'-[(N-BENZYL-N-ISOPROPYL)ALANYL]METHANESULFONANILIDE, m.p. 123.0°–126.0°C. (dec.)(corr.).

Analysis. Calcd. for $C_{20}H_{26}N_2O_3S$: C, 64.14; H, 7.00; N, 7.48. Found: C, 64.21; H, 7.22; N, 7.44.

Compound 17

A mixture of 4'-(2-bromopropionyl)methanesulfonanilide (15.3 g., 0.05 mole) and benzhydrylamine (18.3 g., 0.10 mole) in 200 ml. of acetonitrile is refluxed for a period of 30 hr., cooled and filtered. The product is isolated by concentrating the filtrate to a small volume, diluting with ether, filtering, washing the filtrate with water, drying the washed filtrate over magnesium sulfate, filtering, and acidifying the filtrate with ethanolic hydrogen chloride. The crude hydrochloride salt thus obtained is crystallized from methanol-water to yield analytically pure 4'-[N-(DIPHENYLMETHYL)ALANYL]METHANESULFONANILIDE HYDROCHLORIDE, m.p. 219.0–223.0°C. (dec.)-(corr.)

Analysis. Calcd. for $C_{23}H_{24}N_2O_3 \cdot HCl$: C, 62.08; H, 5.66; N, 6.30. Found: C, 61.90; H, 5.53; N, 6.17.

Compound 18

A mixture of 4'-(2-bromopropionyl)methanesulfonanilide (20 g., 0.07 mole) and cyclopentylamine (11.3 g., 0.132 mole) in 180 ml. of acetonitrile is refluxed for a period of 3 hr., cooled and filtered. The filter cake is stirred with water, filtered and the product free base dried. The free base converted to the hydrochloride salt and crystallized from methanol-isopropyl alcohol provides analytically pure 4'-(N-CYCLOPENTYLALANYL)METHANESULFONANILIDE HYDROCHLORIDE, m.p. 228°–230°C. (dec.)(corr.).

Analysis. Calcd. for $C_{15}H_{22}N_2O_3S \cdot HCl$: C, 51.94; H, 6.68; N, 8.08. Found: C, 51.56; H, 6.82; N, 7.88.

Compound 19

A mixture of 4'-(2-bromopropionyl)methanesulfonanilide (15.3 g., 0.05 mole) and 3,3-diphenylpropylamine (21.1 g., 0.1 mole) in 300 ml. of acetonitrile is stirred for a period of 32 hr., cooled and filtered. The filter cake is washed with acetonitrile, dried, triturated with 500 ml. of water, filtered and dried. The dried filter cake is stirred with 500 ml. of methanol and filtered to provide 12.1 g. of analytically pure 4'-[N-(3,3-DIPHENYLPROPYL)ALANYL]METHANESULFONANILIDE free base, m.p. 158.0°–161.0°C. (dec.)

Analysis. Calcd. for $C_{25}H_{28}N_2O_3S$; C, 68.78; H, 6.46; N, 6.42. Found: C, 68.70; H, 6.59; N, 6.38.

What is claimed is:

1. A process for interrupting pregnancy in a pregnant female mammal capable of resorbing an implanted fertilized ovum comprising orally or parenterally administrating to said mammal an interceptive agent during the interceptive stage in an effective dose to cause resorption of said implanted fertilized ovum and said interceptive agent is an aminoketone of the formula

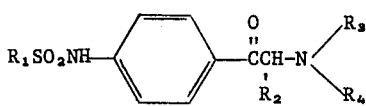

or a pharmaceutically acceptable acid addition salt thereof wherein
  $R_1$ is methyl or ethyl;
  $R_2$ is alkyl of 1 to 3 carbon atoms inclusive,
  $R_3$ is hydrogen, lower alkyl of 1 to 4 carbon atoms inclusive or benzyl;
  $R_4$ is lower alkyl of 1 to 5 carbon atoms inclusive; aralkyl up to 15 carbon atoms inclusive, haloaralkyl up to 15 carbon atoms inclusive; alkyl, 2-propynyl, adamantyl, cycloalkyl of 3 to 6 carbon atoms inclusive; and
  $R_3$ and $R_4$ taken together with nitrogen represents morpholino, thiomorpholino, hexahydro-1H-azepinyl or pyrrolidinyl.

2. The process of claim 1 wherein said effective dose is 20 to 500 mg./kg. body weight.

3. The process of claim 1 wherein said interceptive agent is 4'-[N-(4-chloro-$\alpha,\alpha$-dimethylphenethyl)alanyl]methanesulfonanilide.

4. The process of claim 1 wherein said interceptive agent is 4'-[N-(4-chloro-$\alpha,\alpha$-dimethylphenethyl)alanyl]methanesulfonanilide hydrochloride.

5. The process of claim 1 wherein said interceptive agent is 4'-(N,N-diethylalanyl)methanesulfonanilide.

6. The process of claim 1 wherein said interceptive agent is 4'-(N,N-diethylalanyl)methanesulfonanilide hydrochloride.

7. The process of claim 1 wherein said interceptive agent is 4'-(N-benzyl-N-methylalanyl)methanesulfonanilide.

8. The process of claim 1 wherein said interceptive agent is 4'-(N-benzyl-N-methylalanyl)methanesulfonanilide hydrochloride.

9. The process of claim 1 wherein said interceptive agent is 4'-[2-(hexahydro-1H-azepin-1-yl)propionyl]methanesulfonanilide.

10. The process of claim 1 wherein said interceptive agent is 4'-[2-(hexahydro-1H-azepin-1-yl)propionyl]methanesulfonanilide hydrochloride.

11. The process of claim 1 wherein said interceptive agent is 4'-(N-allyl-N-methylalanyl)methanesulfonanilide.

12. The process of claim 1 wherein said interceptive agent is 4'-(N-isopropyl-N-methylalanyl)methanesulfonanilide.

13. The process of claim 1 wherein said interceptive agent is 4'-[2-(1-pyrrolidinyl)propionyl]methanesulfonanilide.

14. The process of claim 1 wherein said interceptive agent is 4'-(N-tert.-butylalanyl)methanesulfonanilide.

* * * * *